United States Patent [19] [11] 4,007,980
Bracher et al. [45] Feb. 15, 1977

[54] DEVICE FOR THE MEASUREMENT OF THE SIZE OF AN EYE PUPIL

[76] Inventors: Daniel Bracher, Beethovenstrasse 10, 3073 Gumligen; Walter Lotmar, Chaumontweg 102, 3028 Spiegel, near Berne, both of Switzerland

[22] Filed: Aug. 19, 1975

[21] Appl. No.: 605,871

[30] Foreign Application Priority Data

Aug. 23, 1974 Switzerland ............... 11556/74

[52] U.S. Cl. .............................. 351/6; 351/17
[51] Int. Cl.² ........................................ A61B 3/10
[58] Field of Search ........................... 351/6, 17

[56] References Cited
UNITED STATES PATENTS 3,820,879  6/1974  Frisen ..................... 351/6
3,954,329  5/1976  Pomerantzeff ........... 351/6

OTHER PUBLICATIONS

Allen Gonoscope Prism by Bausch & Lomb (1947), pp. 2–5.
Oosterhuis et al., "Binocular Fundus Reflectometry," Ophthal Res. I: pp. 109–123 (1970).

Primary Examiner—Harold A. Dixon
Attorney, Agent, or Firm—Browdy and Neimark

[57] ABSTRACT

A device for measuring the size of an eye pupil, particularly with non-cooperating patients, has a body which contacts the eye and carries on it an illuminating light source, a series of light detectors and an optical system for collecting the divergent light from the illuminating source and directing such light towards the iris of the eye. A stimulus light source can also be included for directing stimulus light through the pupil and onto the retina.

15 Claims, 6 Drawing Figures

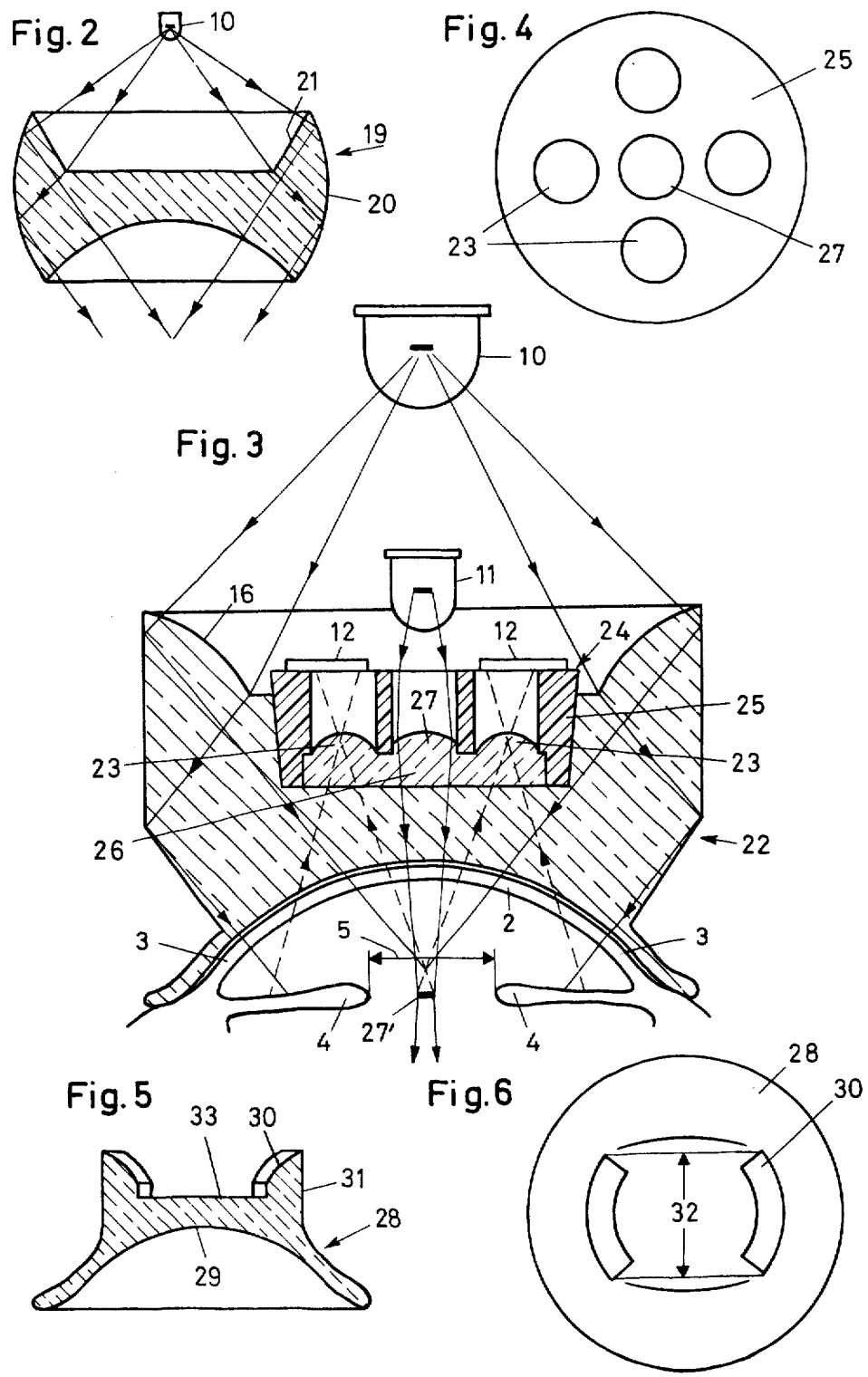

DEVICE FOR THE MEASUREMENT OF THE SIZE OF AN EYE PUPIL

FIELD OF THE INVENTION

The invention relates to a device for the measurement of the size of an eye pupil, comprising at least one light source to illuminate the eye and at least one light detector sensitive to light reflected from the eye.

BACKGROUND OF THE INVENTION

Qualitative or quantitative observation of the pupilary reflex of human subjects, i.e. the variation of the pupil size caused by external stimuli, is of clinical significance because, from a normal or abnormal behavior of this reflex, conclusions can be drawn on the functional state of the brain structures and nerve tracks that participate in stimulus transmission from the locus of stimulation to the muscle bundles regulating the size of the pupil.

Stimuli, apart from optical, may be also acoustical, tactile, thermal or other, thus providing many possibilities to test parts of the neural system. This sort of functional test is most valuable for the clinician when he has to deal with non-collaborating subjects, as, for example, unconscious persons or infants.

Methods for measuring the pupillary reflex of collaborating subjects are known. The subject is told to fixate a target with open eye and the pupil is viewed for example by a cinema or television camera before, during and after application of the stimulus or the eye is illuminated with red or infrared light, and the pupil and the iris are imaged onto a photocell. All known methods are, however, applicable only with difficulty to non-collaborating subjects.

In the case considered here it has to be supposed that the subject, in general, will hold his eyes closed. Nevertheless, his eyeballs may move in an arbitrary and not foreseeable manner. Even when, in such cases, the eyelids were artificially held open, a reliable measurement of the pupil size by known methods would be rendered considerably less accurate, since the pupil would appear distorted by perspective as a consequence of arbitrary eye movements.

SUMMARY OF THE INVENTION

The object of the present invention is a device as mentioned above that enables to illuminate the iris of the eye and to detect light reflected by the iris independently from eye movements, and to prevent at the same time stray light reflected by other surfaces than the iris or by the retina from reaching the detectors.

According to the present invention the device is characterized by an optical system that collects the diverging light beams emitted by the illumination source and directs them towards the iris; it is further characterized by said illumination source, said optical system and said detectors being built into a contact body designed to adhere to the eye and to be moved with the latter.

In such a device said contact body, after being put on the eye, follows each of its movements. It is, moreover, possible to reduce the weight of said body so far that it is readily tolerated by a subject in reclining position. This applies even when a second light source, generating optical stimuli, is incorporated in said body.

Since the optical system according to the present invention makes use only of the more divergent parts of the light emitted by the illumination source, directing them obliquely onto the iris through an annular area of the cornea, there remains free space between the cornea and the illumination source around the optical axis of the eye that can advantageously be used to take up the detector(s) and the stimulus source without any interception of the illuminating light.

Said oblique illumination of the iris includes the additional advantage that those parts of the illuminating light that pass through the pupil will strike lateral parts of the fundus of the eye, from which reflected light will not reach the detector(s) provided to respond to light reflected by the iris.

Since the light-collecting optical system as well as the detector(s) are contained in the contact body adhering to the eye, practically no stray light interfering with the measurement is generated. Relatively strong stray light originates only from optical boundaries between media of high refraction index difference. The detector(s) in the device according to the invention can take up stray light, if any, only from the boundary between the contact body and the cornea. Because there is, however, no air gap between these media, the narrow space being filled with tear or another watery fluid, the index difference is small so that practically no stray light is generated.

FIGS. 1 to 6 show some examples of the present invention.

BRIEF DESCRIPTION OF THE DRAWINGS

FIG. 2 is a variant of the contact body of FIG. 1, shown at a reduced scale;

FIG. 3 is a cross section of another modification of the device;

FIG. 4 is a plan view of body 24 of FIG. 3;

FIG. 5 is a cross section of a contact body that is specially suited to application on prematurely and new-born infants; and FIG. 6 is a plan view of the contact body of FIG. 5.

DESCRIPTION OF PREFERRED EMBODIMENTS

Figure 1:
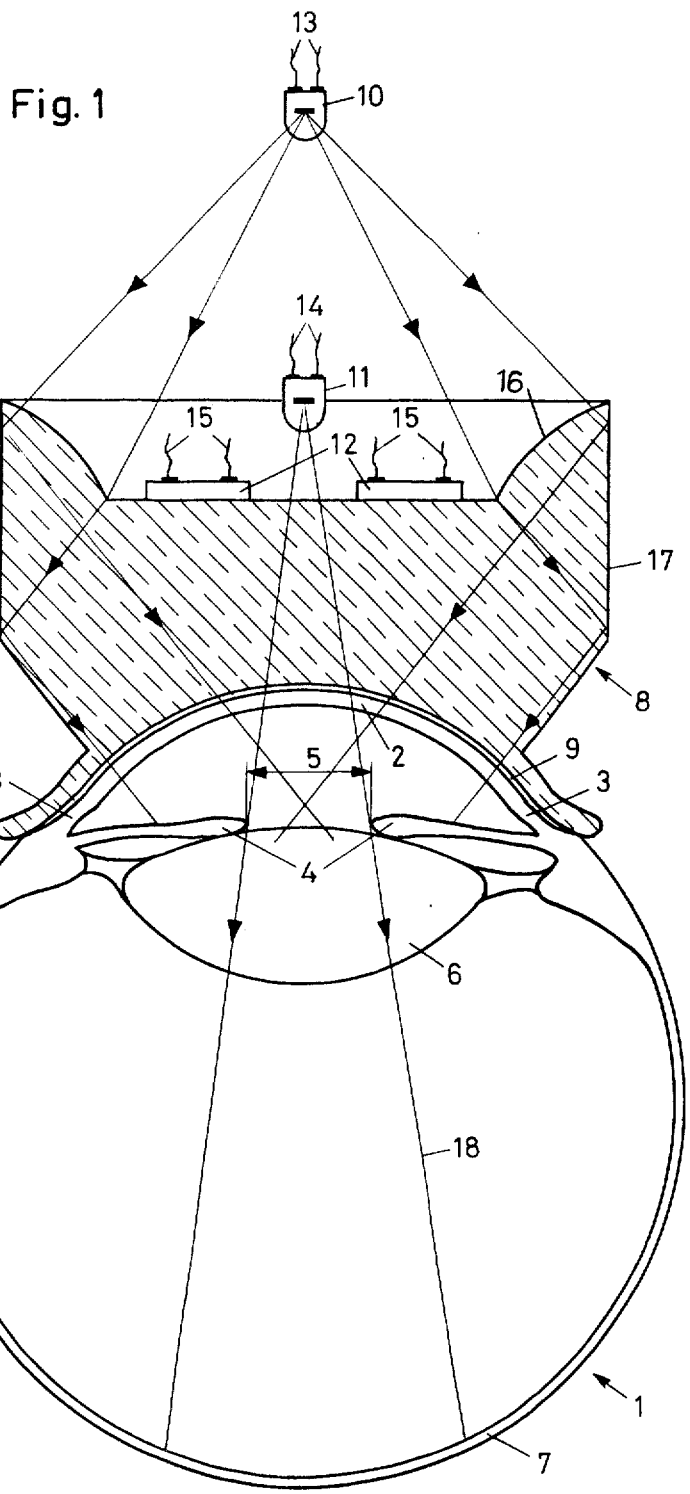
FIG. 1 is a cross section of a first embodiment of the device according to the present invention.

FIG. 1 shows a cross section of an eye-ball 1, with a cornea 2, a conjunctiva 3, an iris 4, a pupil 5, a lens 6, and a retina 7. Adhering to the eye 1 is a contact glass 8 consisting of a transparent material, preferentially a plastic (organic) glass, whose contact surface is adapted to the form of the eye under investigation. Between the eye 1 and the contact glass 8 a thin layer of fluid 9 has been placed in known manner, thus providing optical contact. Two light sources 10 and 11 are rigidly fixed to the contact glass 8, source 10 emitting illumination light and source 11 stimulus light. Also rigidly fixed to the contact glass 8 are several detectors 12, two of them being shown in the figure. The mounts of the light sources and the detectors are not shown, for clarity. Such mounts may, for example, be fixed to a case that can be slid over and fixed to the contact glass 8, said case making, however, no optical contact with those surfaces of the contact glass 8 which act as reflecting surfaces for the illumination light as described below. Electrical leads 13, 14 and 15 for the sources 10, 11 and the detectors 12 are indicated.

Whereas the emission of the stimulus light source 11 must lie within the visible range of the spectrum since the retina 7 is expected to respond to it, the contrary applies to the emission of the light source 10. For the latter, therefore, light that is not perceived by the human eye, e.g. infrared radiation, is suitable. The detectors 12, then, have to be sensitive to this same spectral range. Such a separation of the spectral ranges of the illumination and stimulus lights has the additional advantage that stray light from the stimulus source (if any) may easily be withheld from the detectors 12 by optical filters, not shown.

For the illumination and stimulus light sources 10 and 11 the use of so-called light-emitting diodes is of advantage; these can be obtained commercially. Such diodes, although not being of high intensity, have a relatively small radiating area, which is favorable for the present device. On the other hand their low intensity is compensated by the fact that the light path from the source to the detectors is relatively short.

Nevertheless, it is of interest to use as great a part of the illumination light 10 as possible, in order to make the signal, that is, the variation of the pupil size, as high as possible relative to the unavoidable noise (stray light, instabilities of the detector and the amplifiers). For that purpose the contact glass 8 of the device according to the present invention is conceived as an optical collecting system of a special type which will be described below.

Moreover, it is of advantage to provide not only one but several detectors 12 that may work independently or in series. Miniature photo diodes may be used which are commercially available. Their signals are processed electronically in known manner and may be displayed for example by a pen recorder.

The contact glass 8 of FIG. 1, as an optical system, exhibits a polished toroidal surface 16 and a polished cylindrical surface 17. (The latter may also be given a slightly conical shape if so required by production necessities). The hollow light cone impinging on said refracting toroidal surface 16, emitted by source 10, is collimated and directed towards the iris by total reflection on said polished cylindrical surface 17. The light is thus concentrated on the plane of measurement as defined by the iris 4 and the pupil 5. Part of the light striking the iris 4 is absorbed, another part is diffusely reflected. A certain percentage of the reflected light reaches the detectors 12 and is recorded. If now the size of the pupil changes, e.g. as a reaction to a light stimulus reaching the retina 7 from the source 11 in the form of the beam 18, the surface of the iris lying within the illuminated area, and therefore the amount of reflected light, change too. The signals of the detectors thus vary as to sign and quantity according to the variation of the pupil size, and their temporal course can be recorded. Any movements of the eye 1 do not influence the results of the measurement because the contact glass 8 and hence all measuring elements as described take part in such movements.

Good adherence of the contact glass 8 to the eye 1 can be provided in known manner by slight suction. The bore channel of small diameter necessary for this is not shown in FIG. 1.

Another form 19 of the contact glass is shown in FIG. 2. Here the functions of the collimating and the totally reflecting surfaces 16 and 17 of FIG. 1 are taken over by one single polished toroidal mantle surface 20, whereas the entrance surface 21 for the light from source 10 is conical.

FIG. 3 shows a third variant of the contact glass. The contact glass 22 differs from the contact glass 8 of FIG. 1 insofar as lenses 23 are provided, each lens forming an image of a certain sector of the iris 4 on one of the detectors 12. In contrast to this, light reflected from any point of the iris can reach all the detectors in the case of FIG. 1. With the device of FIG. 3 it is therefore possible to differentiate the pupillary reaction in respect to certain sectors of the iris. This too is of clinical interest since the coordination of the various muscle bundles responsible for iris movements may be out of order.

According to FIG. 3 the lenses 23 of the contact glass 22 are part of a removable body 24. If required, the body 24 may be exchanged for another piece without such lenses. Said body 24 consists of a mount 25 that may be formed, for example, out of an opaque plastic material. This mount serves as a support for a lens body 26 of transparent material, e.g. glass or transparent plastic. The lenses 23 may be given an aspherical form. The detectors 12 are located above the lenses 23 on the upper surface of mount 25. The lens body 26 comprises, in addition, a central lens 27 that serves to direct the stimulus light from source 11 towards the retina (not shown here, see FIG. 1) through the pupil 5. The advantage of providing such a lens is that it can be devised to form an image 27' of the small radiating area of source 11 in the pupil plane, as shown. Since that image will be smaller than the smallest diameter the pupil is able to contract to, the retinal area covered by the stimulus light will be independent of the pupil size, whereas for the device of FIG. 1 it does depend on that size; this is not desirable, however, for well-defined investigations.

As for the rest, the contact glass 22 of FIG. 3 corresponds to the contact glass 8 of FIG. 1, especially so concerning the course of the light beams from source 10 to iris 4.

As can be seen on the plan view, FIG. 4, of body 24 (without detectors 12), four lenses 23 may be provided, for example.

The use of the device described above in several examples is made difficult or impossible when measurements on prematurely or newly born infants are intended, because in these instances the lid fissure is too small to adapt the cylindrical optical system of the contact glass as shown in FIGS. 1 to 3. In FIGS. 5 and 6 a modification of the contact glass is shown that avoids this difficulty. The contact glass 28 possesses a cup-like contact part 29 of similar form to those described above, except that its radius is smaller, thus being adapted to the smaller radius of infantile corneas. The cross section (FIG. 5) of the optical system collecting the light from the illumination source (not shown) is of the same form as that of the contact glasses described above in FIGS. 1 and 3; that is, there is a collimating toroidal surface 30 and a totally reflecting cylindrical surface 31. However, as shown in FIG. 6, the part of the contact glass delimited by these two surfaces is partially cut off. The remaining sectors of the optical system have a width 32 of 5.5 mm, for example, which conforms to the lid fissure of prematurely or new-born infants. Besides, the contact glass 28, like that of FIG. 3, is provided with a recess 33 into which a body with lenses of appropriate dimensions may be fitted, as shown in FIG. 3. Other parts of the device, especially the illumination source and the detectors, not shown in FIGS. 5 and 6, correspond to those described above. Experience has shown that with the device described, measurements of the pupil size on prematurely and new-born infants are possible.

It will be obvious to those skilled in the art that various changes may be made without departing from the scope of the invention and the invention is not to be considered limited to what is shown in the drawings and described in the specification.

What is claimed is:

1. A device for measuring the size of an eye pupil, comprising:
    contact body means made of a transparent material, for adhering to and moving with the eye;
    illuminating light source means, fixedly connected to said contact body means, for directing illuminating light divergently towards the eye;
    light detection means, fixedly connected to said contact body means, for detecting light reflected by the eye; and
    optical system means, integral with said transparent contact body means, for collecting the diverging light from said illuminating light source means and directing the collected light obliquely onto the iris, the light converging towards the optical axis of the eye through an annular area of the cornea,
    whereby light impinging on the iris is reflected toward said light detection means and light passing through the pupil does so obliquely and thus strikes only lateral parts of the fundus of the eye, from which reflected light will not reach said light detection means.

2. A device in accordance with claim 1 wherein said optical system means includes a refracting toroidal collecting surface and a totally reflecting surface, whereby the diverging light is collected through said toroidal collecting surface and directed toward said reflecting surface from which the light is reflected in said oblique fashion onto the iris.

3. A device in accordance with claim 2 wherein said totally reflecting surface is at least approximately cylindrical.

4. A device in accordance with claim 2 wherein said totally reflecting surface is conical.

5. A device in accordance with claim 1 wherein said optical system means includes a refracting conical surface and a collecting, toroidal, totally reflecting surface, whereby the diverging light passes through said refracting surface and is collected by said reflecting surface from which the light is reflected in said oblique fashion onto the iris.

6. A device in accordance with claim 1 wherein said illuminating light source means is for illumination of the eye with invisible light.

7. A device in accordance with claim 7 wherein said invisible light is infrared.

8. A device in accordance with claim 1 wherein said illuminating light source means comprises a quasi-punctiform light-emitting diode.

9. A device in accordance with claim 1 wherein said light detector means comprises a photo diode.

10. A device in accordance with claim 1 wherein said transparent material contact body means and optical system means are made of glass or plastic.

11. A device in accordance with claim 1 further including a stimulus light source means, fixedly connected to said contact body, for illuminating the retina through the pupil of the eye.

12. A device in accordance with claim 1 wherein two opposite sectors of said optical system means are cut out.

13. A device in accordance with claim 1 wherein said light detector means comprises a plurality of light detectors, mounted symmetrically about the central axis.

14. A device in accordance with claim 13 further including a body removably connected to said contact body with several lenses, each of said lenses forming an image of a sector of the iris on the sensitive surface of one of said light detectors, the detectors being fastened to the upper surface of said removable body.

15. A device in accordance with claim 14 further including a stimulus light source means, fixedly connected to said contact body, for illuminating the retina through the pupil of the eye, and wherein said removable body carries a collecting lens arranged in the path of light from said stimulus light source means.

* * * * *